United States Patent [19]
Mizobuchi et al.

[11] Patent Number: 5,718,889
[45] Date of Patent: Feb. 17, 1998

[54] BASIC ZINC CARBONATE-ACTIVATED CARBON DEODORANT

[75] Inventors: Manabu Mizobuchi, Nara; Tadao Kawamura, Osaka; Kazuhiro Matsuura, Fukui; Takaharu Nakagawa; Toshiyuki Yamauchi, both of Osaka, all of Japan

[73] Assignee: Matsushita Electric Works, Ltd., Kadoma, Japan

[21] Appl. No.: 619,209

[22] Filed: Mar. 21, 1996

[30] Foreign Application Priority Data

Mar. 28, 1995 [JP] Japan ................. 7-070128

[51] Int. Cl.⁶ .............. A61K 7/32; A61K 7/36; A61K 7/00
[52] U.S. Cl. .............. 424/65; 424/67; 424/400; 424/401
[58] Field of Search .............. 424/68, 67, 400, 424/401

[56] References Cited

FOREIGN PATENT DOCUMENTS 0 643 014 A1  3/1995  European Pat. Off. .

OTHER PUBLICATIONS

Patent Abstracts of Japan; JP-A-62 152462; Jul. 7, 1987.
Patent Abstracts of Japan; JP-A-07-313867; vol. 95, No. 012, Dec. 1995.
Patent Abstracts of Japan; JP-A-01-171556; vol. 013, No. 447, Jul. 1989.
Patent Abstracts of Japan; JP-A-06-225997; vol. 018, No. 597, Aug. 1994.
Patent Abstracts of Japan; JP-A-06-070871; vol. 018, No. 316, Mar. 1994.

*Primary Examiner*—Shelley A. Dodson
*Attorney, Agent, or Firm*—Armstrong, Westerman, Hattori, McLeland & Naughton

[57] ABSTRACT

A deodorant composition comprises an activated carbon, a binder, an argillaceous material, and a basic zinc carbonate. A deodorant is manufactured by the following steps: (a) a mixing step of the composition materials, (b) a kneading step to knead the mixture, (c) an extrusion to shape the kneaded mixture into a honeycomb structured solid or a powder, and (d) a drying step to remove moisture from the solid. The honeycomb structured deodorant has excellent odor absorption particularly for odors, hydrocarbons, and nitrogen oxides in vehicle exhausts.

5 Claims, 1 Drawing Sheet

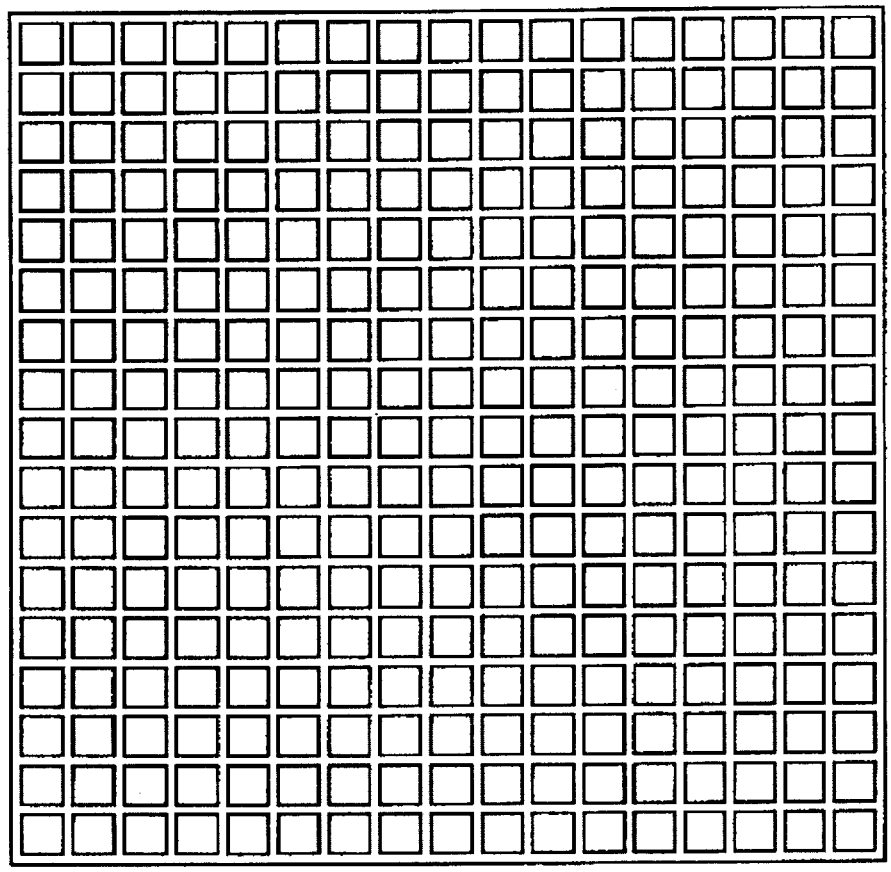
FIGURE

BASIC ZINC CARBONATE-ACTIVATED CARBON DEODORANT

BACKGROUND OF THE INVENTION

1. Field of the Invention

The preset invention is related to a deodorant composition comprising an activated carbon, a binder, an argillaceous material, and a basic zinc carbonate and a manufacturing process of a deodorant from the deodorant composition including a mixing step, a kneading step, an extruding step, and a drying step. The deodorant is used to remove odors, hydrocarbons, and nitrogen oxides (NOx) from automobile and truck exhausts and various odors from homes, buildings, and industries.

2. The Prior Art

Odors are unpleasant to our sense of smell, namely, hydrogen sulfide, methyl mercaptan, ammonia, trimethyl amine, methyl sulfide, acetaldehyde, styrene, propionic acid, n- and iso-valeric acids, butyric acid, formaline, acrolein, acetic acid, methyl amine, dimethyl amine, hydrocarbons, and NOx. These odors are generated from garbage boxes, refrigerators, toilets, trucks, and automobiles; in hotels, restaurants, hospitals, and industries.

In order to deal with unpleasantness of the odors, a variety of deodorants are manufactured. A masking deodorant is an aromatic compound of strong fragrance which is sprayed to cover up (or mask) an odor. An adsorption deodorant is typically an activated carbon having a deodorant mechanism of which odor molecules are adsorbed in fine pores provided on particle surfaces of the carbon. A neutralizing deodorant is either an acid or base which suppresses the unpleasantness of an odor by neutralizing the odor. And an ozone deodorant, disclosed in Japanese Early Patent Publication (KOKAI) 5-49862, adds an ozone gas to an odor so as to oxidize the odor for the suppression of the unpleasantness of odor.

Among the deodorants described above, an adsorption deodorant of activated carbon is widely used to remove not only the odors listed above but also hydrocarbons and NOx from automobile and truck exhausts. The activated carbon deodorant is made typically from a deodorant composition comprising a carbon, a binder, and a plasticizer.

Since government environmental regulations for emission of hydrocarbons and NOx are implemented more strictly in the future around the world, it is always desired to manufacture an activated carbon deodorant having superior deodorant ability against the environmentally unsafe gases, especially, for countries which allow a significant number of diesel vehicles.

In addition to the necessity of the deodorant ability, a desired deodorant is needed to be manufactured at low cost. A conventional manufacturing process of the activated carbon deodorant consists of the following steps: (a) mixing a carbon powder with a binder and a plasticizer, (b) kneading the resultant mixture, (c) extruding of the kneaded mixture into a solid, (d) activating of the extruded solid, and (e) drying the solid. However, a problem arises in the activation step since it is required to install large and expensive activation equipment for providing fine pores on particle surfaces of the extruded solid, resulting in costly investment.

Moreover, a desired activated carbon deodorant is shaped into various forms such as a honeycomb structure to enhance the deodorant ability. Nevertheless, in the extruding step, a kneaded mixture is extruded unsmoothly into a honeycomb structured solid; as a result, cracks or breaks often present in a dried solid.

SUMMARY OF INVENTION

The invention is related to a deodorant composition comprises an activated carbon of 100 parts, a binder of 1–40 parts, an argillaceous material of 3.5–47, a basic zinc carbonate of 1–33 parts and a manufacturing process of the invented deodorant consists of (a) a mixing step to mix an activated carbon, an binder, an argillaceous material, and a basic zinc carbonate, (b) a kneading step to blend the mixture thoroughly, (c) an extruding step of the kneaded mixture into a solid, and (d) a drying step to remove moisture from the solid. The feature of the invention is the use of the basic zinc carbonate to the conventional activated carbon deodorant.

An object of the present invention is to provide an activated carbon deodorant having excellent deodorant ability particularly for removing odors, hydrocarbons, and NOx from vehicle exhausts.

Another object of the present invention is to provide a manufacturing process which is simpler than the conventional process. The manufacturing process in the invention requires no need of the activation after the extrusion and employs an activated carbon, instead of a carbon, in the mixing step. This simplification on the manufacturing process leads to reduction of manufacturing cost.

Another object of the present invention is to improve moldability in the extrusion.

BRIEF EXPLANATION OF DRAWING

FIGURE illustrates a front view of a honeycomb structured deodorant comprising an activated carbon, a binder, and an argillaceous material, and a basic zinc carbonate.

DESCRIPTION OF PREFERRED EMBODIMENTS

The present invention is directed to a deodorant composition comprising an activated carbon, a binder, an argillaceous material used as a plasticizer, and a basic zinc carbonate and the manufacturing process of a deodorant which consists of the following steps: a) mixing an activated carbon, a binder, an argillaceous material, and a basic zinc carbonate, b) kneading the resultant mixture, c) extruding the kneaded mixture into a solid, and d) drying the solid. A preferred structure of the invented deodorant is honeycomb or pellet. A honeycomb structured deodorant is illustrated in FIGURE.

Activated carbons are prepared from carbon rich materials such as coconut shells, coals, sugars, lumbers, lignites, peats, and phenol resins. These materials are heated at several hundred degrees centigrade in order for production of carbon powders; and the carbon powders are treated with an activation process by steam, gas (involving carbon dioxide, oxygen, and the like), or chemical (involving zinc chloride, phosphoric acid, dehydrating agents, and oxidizing agents) activations. These activation processes provides submicron pores on particle surfaces of the carbon powder, and each of the pores has a pore diameter. It is preferred to use the steam activation.

An accumulative pore volume is defined as a total of volumes of pores of an activated carbon. The volumes of pores are calculated by B. J. H. (Barrett, Joyer, and Halenda) method (Journal of the American Chemical Society, 73,373 (1951)). A preferred accumulative pore volume per gram of the steam activated carbon having a pore diameter less than 30 Å is 0.2 cc or more.

An activated carbon powder is shifted with a sieve having 200 meshes per inch$^2$ in order to separate fine activated carbon particles from granular activated carbon particles.

It is preferred to use a steam activated carbon which is made from coconut shells and coals, is shifted with the sieve, and has its 0.2 cc or more accumulative pore volume per gram of the activated carbon having a pore diameter less than 30 Å.

A basic zinc carbonate is $2\ ZnCO_3 \cdot 3Zn(OH)_2 \cdot H_2O$. The carbonate is added to enhance the deodorant ability and to improve moldability of an extruded solid deodorant.

A binder is chosen at least one of the following water soluble organic materials: methyl cellulose, carboxyl methyl cellulose, polyvinyl alcohol, and starch paste. It is preferred to use methyl cellulose. The binder is used to shape the deodorant composition mixture easily into a honeycomb structured solid during the extruding step and keeps the solid shape during the drying step.

A suitable amount of water may be employed with the binder.

A argillaceous material is used as a plasticizer and chosen at least one of the following: kibushi clay, gairome clay, kaolinite, and bentonite. The argillaceous materials are employed essentially to stabilize the honeycomb structure to enhance the moldability.

Kaolinite is a basic aluminum silicate mineral of $Al_2Si_2O_5(OH)_4$. Kibushi clay is basically a kaolinite including charcoal particles. Gairome clay is a grayish green kaolinite having substantially quarts particles having a diameter from 1 to 3 mm. And bentonite is a highly colloidal plastic clay composed largely of montmorillonite clay minerals.

Suitable amounts of zinc oxide and aluminum silicate may be added to the deodorant composition described above.

An amount of the basic zinc carbonate is preferred to be 1–33 parts based on the activated carbon of 100 parts. If an amount of the basic zinc carbonate used is less than 1 part, then it is possible for the deodorant to loose its proper deodorant ability. If the amount is more than 33 parts, then the moldability for which a kneaded deodorant composition mixture is shaped into a honeycomb structure or a pellet can be damaged.

An amount of the binder is preferred to be 1–40 parts based on the activated carbon of 100 parts.

An amount of the argillaceous material is preferred to be 3.5–47 parts based on the activated carbon of 100 parts. If an amount of the argillaceous material used is less than 3.5 parts then, it is difficult to maintain a fine honeycomb structure and a pellet form after the extrusion of a kneaded deodorant composition mixture. If the amount is more than 47 parts, then an amount of an activated carbon used is reduced in resulting loss of the deodorant ability.

The manufacturing process of the invented deodorant consists of (a) a mixing step to combine an activated carbon, a binder, an argillaceous material, and a basic zinc carbonate, (b) a kneading step to blend the mixture thoroughly, (c) an extrusion of the kneaded mixture into a solid, and (d) a drying step to remove moisture from the solid.

In the drying step, the moisture of the solid can be removed by a microwave oven.

The invented deodorant removes odors such as hydrogen sulfide, methyl mercaptan, ammonia, trimethyl amine, methyl sulfide, acetaldehide, styrene, propionic acid, n- and iso-valeric acids, butyric acid, formaline, acrolein, acetic acid, methyl amine, and dimethylamine. In particular, the deodorant removes effectively odors, hydrocarbons, and NOx from automobile and truck exhausts.

The basic zinc carbonate-activated carbon deodorant in accordance herewith provides improvement of the deodorant ability, improvement of the moldability of the honeycomb structured deodorant, and simplification of the manufacturing process for the manufacturing cost reduction.

EXAMPLES 1–6

An activated carbon made from coals (100 parts) was mixed with a methyl cellulose (3.9 parts), an argillaceous material (19.5 parts), a basic zinc carbonate (6.5 parts) in a container. The mixture was knead in the container for 2 hours. Then the kneaded mixture was extruded into a honeycomb structured solid. The solid was dried to remove moisture by using a microwave oven. As mentioned earlier, the honeycomb structured deodorant was described in FIGURE.

Deodorants in EXAMPLES 2–6 were prepared in the same process explained above, but only differences are amounts of the ingredients. These amounts are shown in the following table.

TABLE I

|  | EXAMPLE 1 | EXAMPLE 2 | EXAMPLE 3 | EXAMPLE 4 | EXAMPLE 5 | EXAMPLE 6 |
|---|---|---|---|---|---|---|
| Coconut shell activated carbon | 100 | 100 | 100 | 100 | 100 | 100 |
| Basic zinc carbonate | 6.5 | 21.3 | 32.3 | 13.3 | 2.8 | 2.9 |
| Kibushi Clay | 19.5 | 21.6 | 6.2 | 19.9 | 35.4 | 25.7 |
| Methyl cellulose | 3.9 | 4.4 | 15.4 | 4.1 | 8.8 | 14.3 |

One of the deodorants made filtered an exhaust gas from a diesel generator having its space velocity SV of 170,000 [1/h]. The space velocity is defined as exhaust flow rate/honeycomb volume. Then, six persons smelled the filtered exhaust to evaluate a degree of the unpleasantness of odor based on odor strength levels which correspond sensitivities of smell shown in the following TABLE II.

TABLE II

| | Odor strength level |
|---|---|
| 0 | None |
| 1 | Subtle |
| 2 | Slight |
| 3 | Fair |
| 4 | Strong |
| 5 | Harsh |

The odor test explained above was performed on the other deodorants. Results of the odor tests for six examples were taken; the lowest and the highest results were discarded; and the remaining results were averaged. The averaged values for the examples are listed in TABLE III.

Moldability of the deodorant composition is evaluated based on easiness in the extruding a kneaded deodorant mixture into a honeycomb structured solid and the absence of deformations and, from these qualities, is ranked with the following levels: good for excellent smooth extrusion and the absence of deformations, fair for fine smooth extrusion and the presence of slight deformations, and poor for difficult extrusion and the presence of significant deformations.

TABLE III

|  | EXAMPLE 1 | EXAMPLE 2 | EXAMPLE 3 | EXAMPLE 4 | EXAMPLE 5 | EXAMPLE 6 |
| --- | --- | --- | --- | --- | --- | --- |
| Odor strength level | 2.5 | 1.7 | 1.9 | 2.0 | 2.6 | 2.6 |
| Moldability | good | good | fair | good | good | good |

COMPARATIVE EXAMPLE 1

In this comparative example, no basic zinc carbonate was used. An odor strength level for the deodorant in this preparation was 3.5 which was clearly higher than those for the deodorant in the examples 1–6 although the moldability of this deodorant is as good as the deodorants in the examples 1–6. Thus, comparing this result with the results in these examples, it follows that the addition of the basic zinc carbonate improves deodorant ability.

COMPARATIVE EXAMPLE 2

An excess of basic zinc carbonate was used. However, a honeycomb structured deodorant was extremely difficult to make due to instability for the honeycomb structure.

COMPARATIVE EXAMPLE 3

No argillaceous material was used. As a result, a honeycomb structured deodorant was extremely difficult to make due to instability for the honeycomb structure.

COMPARATIVE EXAMPLE 4

No methyl cellulose, a binder, was used. As a result, a honeycomb structured deodorant was extremely difficult to make due to instability for the honeycomb structure.

Amounts of the deodorant ingredients for these comparative examples are shown in TABLE IV, and their evaluations for the moldability and structure stability are shown in TABLE V.

TABLE IV

|  | Comparative example 1 | Comparative example 2 | Comparative example 3 | Comparative example 4 |
| --- | --- | --- | --- | --- |
| Coconut shell activated carbon | 100 | 100 | 100 | 100 |
| Basic zinc carbonate | 0 | 43.5 | 11.9 | 30.5 |
| Kibushi Clay | 37.0 | 25.2 | 0 | 22.1 |
| Methyl cellulose | 15.2 | 5.2 | 7.1 | 0 |

TABLE V

|  | Comparative example 1 | Comparative example 2 | Comparative example 3 | Comparative example 4 |
| --- | --- | --- | --- | --- |
| Odor strength level | 3.5 | — | — | — |
| Moldability | good | poor | poor | poor |

The deodorants prepared in accordance herewith the experimental process described above have excellent deodorant ability and moldability. It is produced at less cost since the activation is done before the mixing step and the steam activated carbon can be used at the mixing step.

What is claimed is:

1. A deodorant composition comprising:

100 parts of an activate carbon, said activated carbon having submicron pores in a surface thereof;

1–40 parts of a binder, said binder being at least one selected from the group consisting of methyl cellulose, carboxyl methyl cellulose, polyvinyl alcohol, and starch paste;

3.5–47 parts of an argillaceous material, said argillaceous material being at least one selected from the group consisting of kibushi clay, gairome clay, kaolinite, and bentonite; and 1–33 parts of a basic zinc carbonate.

2. The deodorant composition of claim 1, wherein said activated carbon is made by steam-activating a carbon material in order to provide submicron pores on surfaces of the activated carbon; said submicron pores have a pore diameter; an accumulative pore volume per gram of said activated carbon, which is defined as a total of pore volumes of said activated carbon per gram of said activated carbon, having a pore diameter less than 30 Å is 0.2 cc or more.

3. A process of preparing said deodorant of claim 1 comprising the following steps:

(a) mixing said activated carbon, said binder, said argillaceous material, and said basic zinc carbonate;

(b) kneading the resulting mixture;

(c) molding the kneaded mixture into a solid; and (d) drying said solid.

4. The deodorant of claim 1, wherein said activated carbon is made from a coal.

5. The deodorant of claim 1, wherein said activated carbon is made from a coconut shell.

* * * * *